United States Patent
Wu et al.

(10) Patent No.: US 9,470,749 B2
(45) Date of Patent: Oct. 18, 2016

(54) TEST APPARATUS WITH DRY ENVIRONMENT

(71) Applicant: CHROMA ATE INC., Tao-Yuan (TW)

(72) Inventors: Xin-Yi Wu, Tao-Yuan-Hsien (TW); Hsuan-Jen Shen, Tao-Yuan (TW); Chien-Ming Chen, Tao-Yuan (TW); Chin-Yi Ou Yang, Tao-Yuan (TW)

(73) Assignee: CHROMA ATE INC., Tao-Yuan Hsien (TW)

( * ) Notice: Subject to any disclaimer, the term of this patent is extended or adjusted under 35 U.S.C. 154(b) by 423 days.

(21) Appl. No.: 14/108,176

(22) Filed: Dec. 16, 2013

(65) Prior Publication Data
US 2014/0182397 A1 Jul. 3, 2014

(30) Foreign Application Priority Data

Dec. 27, 2012 (TW) .............................. 101150472 A

(51) Int. Cl.
*G01R 31/28* (2006.01)
*G01N 1/42* (2006.01)
(52) U.S. Cl.
CPC ............. *G01R 31/2877* (2013.01); *G01N 1/42* (2013.01); *G01R 31/2865* (2013.01)
(58) Field of Classification Search
None
See application file for complete search history.

(56) References Cited

U.S. PATENT DOCUMENTS

| 7,078,923 B2* | 7/2006 | Dejima .................... 324/750.03 |
| 7,595,630 B2* | 9/2009 | Shi et al. ................. 324/750.23 |
| 2008/0186043 A1* | 8/2008 | Beaman et al. ............. 324/763 |
| 2013/0206383 A1* | 8/2013 | Maeda et al. ................ 165/253 |
| 2014/0338470 A1* | 11/2014 | Lehman et al. ............. 73/865.6 |

* cited by examiner

*Primary Examiner* — Robert R Raevis
(74) *Attorney, Agent, or Firm* — Muncy, Geissler, Olds & Lowe, P.C.

(57) ABSTRACT

A test apparatus includes a test site, a buffer carrying device, a transport carrying device, a handling mechanism and a dry air flow guide mechanism. The test site performs a test procedure on the objects. The buffer carrying device is disposed close to a side of the test site, holds the objects and performs a temperature conditioning process. The transport carrying device is disposed close to another side of the test site, moves back and forth along a transporting direction, transports the objects into and out of the test site, and heats up the objects. The handling mechanism carries the objects among the buffer carrying device, the test site and the transport carrying device. The dry air flow guide mechanism guides a dry air to surround the test site, the buffer carrying device, the transport carrying device and the handling mechanism and generates a dry environment to prevent dew condensation.

7 Claims, 11 Drawing Sheets

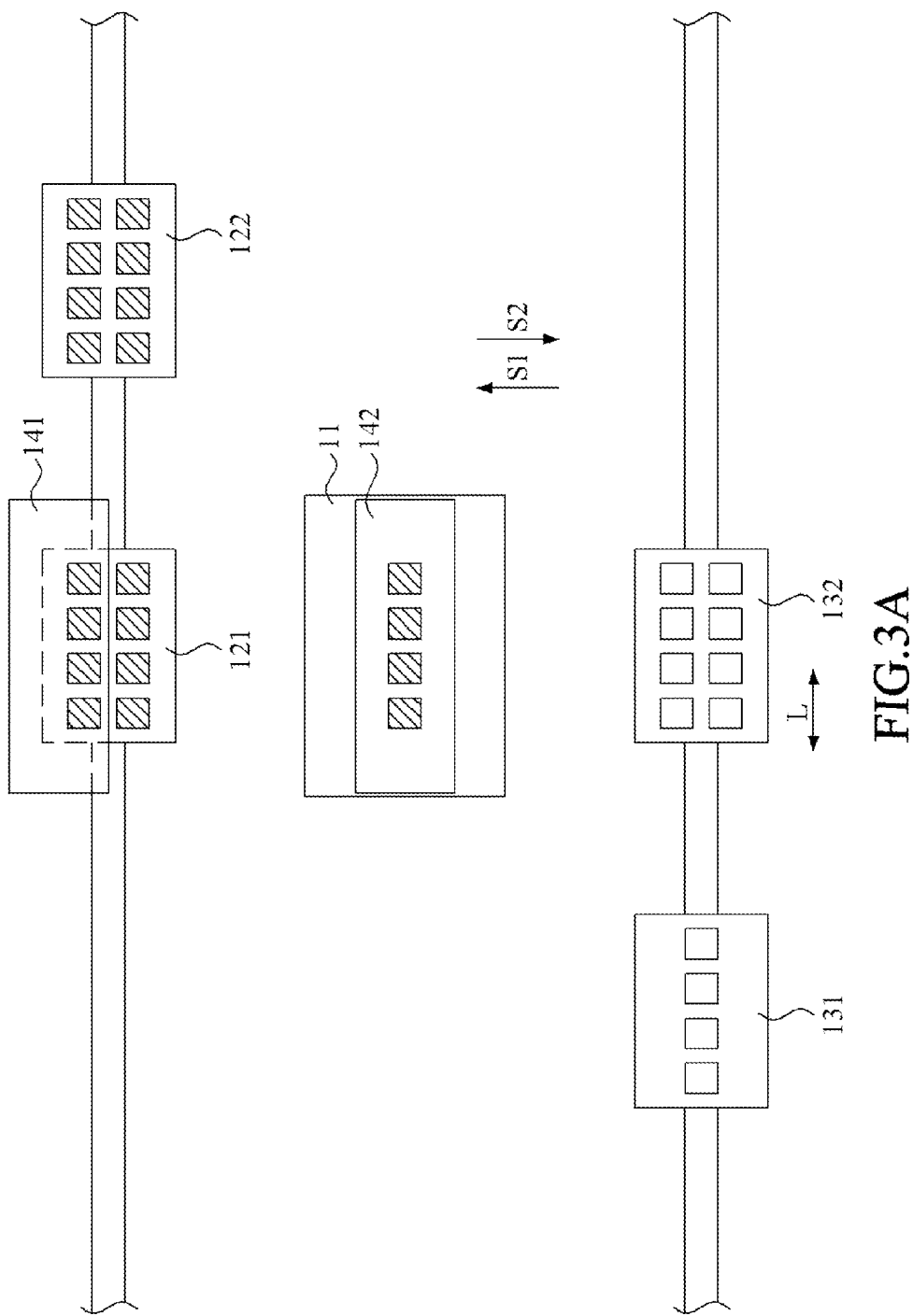

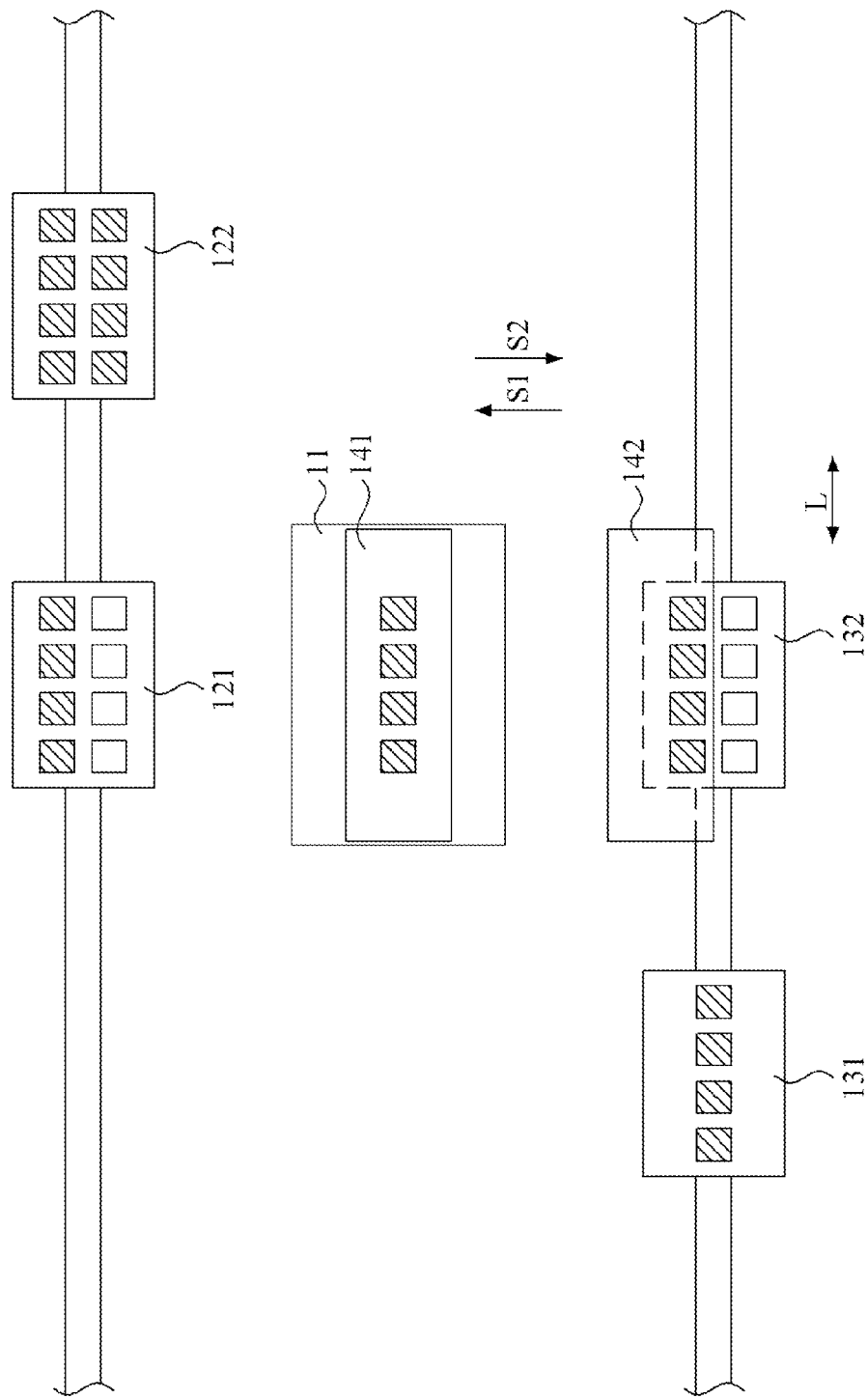

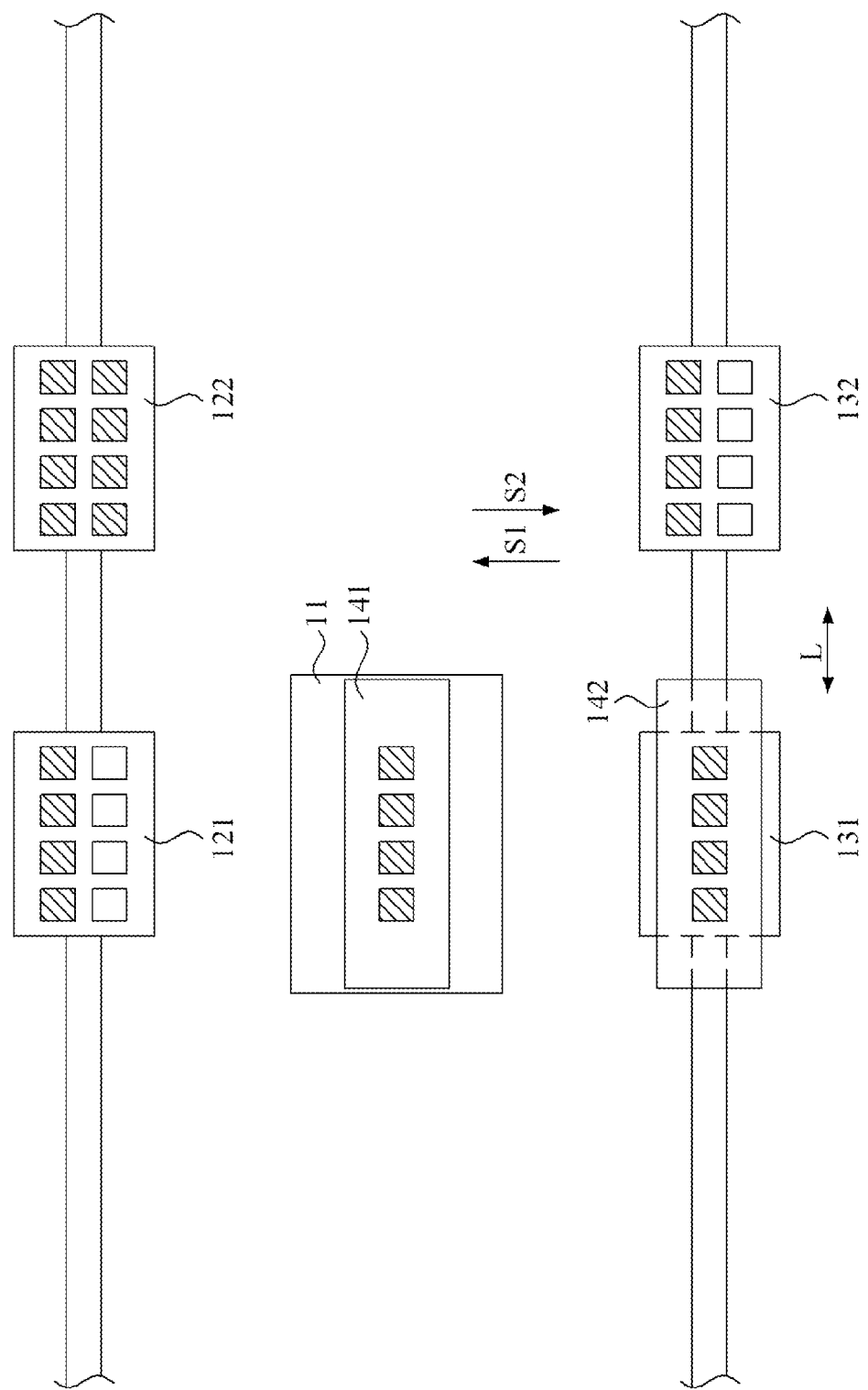

TEST APPARATUS WITH DRY ENVIRONMENT

This application claims the benefits of the Taiwan Patent Application Serial NO. 101150472 filed on Dec. 27, 2012, the subject matter of which is incorporated herein by reference.

BACKGROUND OF THE INVENTION

1. Field of the Invention

The present invention relates to a test apparatus with dry environment and more particularly, relates to a test apparatus with dry environment and performing a temperature conditioning process.

2. Description

Due to the development of science and technology, the electronic devices have been developed rapidly, which improves the life standards of human beings. Integrated circuits (IC) are not only widely used as the components in the electronic devices but also in vehicles and other aspects of human life. Since IC components are very important in electronic devices, its reliability becomes vital when it comes to endurance.

For example, since mobile devices such as cell phones or tablet computers and vehicles need to be operable in low temperatures for arctic countries, whether IC components can operate normally in cold weather becomes a relatively vital issue. As a result, testing IC components in low temperature has become a necessary test requirement in recent years. Among current low temperature tests, there is a way of filling the internal of the test apparatus with Nitrogen air to build up an environment of low temperature for the IC components to be tested in low temperature.

However, when performing such a test, people will have to wait until the test apparatus is in low temperature and until objects to be tested also cools down to temperature suitable for test. Thus, a lot of time is wasted in waiting for the right temperature. Besides, since the temperature of the ambient environment of the factory is higher than the testing temperature, the test apparatus needs to be isolated completely. If adjustment or maintenance is required, or if the test is completed, people will have to wait until the temperature of the test apparatus has raising above the temperature of the ambient environment; otherwise, dew condensation or even icing will occur on the tested IC components or internal components of the test apparatus, which is very inconvenient and needs to be improved.

SUMMARY OF THE INVENTION

In prior art, when performing a low temperature test, people will have to wait until the test apparatus is in low temperature and until objects to be tested also cools down to temperature suitable for test. Thus, a lot of time is wasted in waiting for the right temperature. Besides, since the temperature of the ambient environment of the factory is higher than the testing temperature, the test apparatus needs to be isolated completely. If adjustment or maintenance is required, or if the test is completed, people will have to wait until the temperature of the test apparatus has rising above the temperature of the ambient environment; otherwise, dew condensation or even icing will occur on the tested IC components or internal components of the test apparatus, which is very inconvenient.

Therefore, a test apparatus with dry environment is provided which can regulate the temperature and generates a dry environment for test, which saves time for awaiting the right temperature and prevents the IC components from dew condensation or even icing.

A test apparatus with dry environment for testing a plurality of objects is provided according to embodiments of the present invention. The test apparatus comprises a test site, a buffer carrying device, a transport carrying device, a handling mechanism and a dry air flow guide mechanism. The test site performs a test procedure on the objects. The buffer carrying device is disposed close to a side of the test site, holds the objects and performs a temperature conditioning process on the objects. The transport carrying device is disposed close to another side of the test site and is disposed movably back and forth along a transporting direction, the transport carrying device transporting the objects into and out of the test site and performing a temperature recovery process on the objects until they reaching an ambient temperature. The handling mechanism carries the objects to the buffer carrying device, to the test site and to the transport carrying device. The dry air flow guide mechanism guides a dry air to surround the test site, the buffer carrying device, the transport carrying device and the handling mechanism and generates a dry environment to prevent dew condensation.

The handling mechanism comprises a first carrying arm and a second carrying arm; the first carrying arm carrying the objects from the transport carrying device to the buffer carrying device for the temperature conditioning process, carrying the objects from the buffer carrying device to the test site for the test procedure, and carrying the objects from the test site to the transport carrying device for the heat-up; the second carrying arm carrying the objects from the transport carrying device to the buffer carrying device for the temperature conditioning process, carrying the objects from the buffer carrying device to the test site for the test procedure, and carrying the objects from the test site to the transport carrying device for the heat-up. When the first carrying arm moves from the transport carrying device to the buffer carrying device, the second carrying arm stays at the test site for the test procedure and waits; when the first carrying arm moves from the buffer carrying device to the test site, the second carrying arm moves from the test site to the transport carrying device.

The transport carrying device comprises a position mechanism, an input holding part and an output holding part; the position mechanism performing a position adjustment on the objects; the handling mechanism carrying the objects from the input holding part to the buffer carrying device for the temperature conditioning process and carrying the objects from the test site to the output holding part for the heat-up. The output holding part comprises a heat-up device performing the temperature recovery process. Besides, the buffer carrying device comprises a plurality of holding parts and moves back and forth along the transporting direction for the handling mechanism carrying the objects to the holding parts individually and comprises a temperature controller performing the temperature conditioning process.

Compared with prior art, the test apparatus according to embodiments of the present invention can perform the temperature conditioning process and has a dry environment for test. Therefore, the temperature of the objects has been conditioned before tests, which saves time for waiting the objects to be cooled. Besides, the dry air flow guide mechanism creates a dry environment for the test apparatus to prevent dew condensation and icing. Moreover, the test apparatus further comprises the function of heat-up so the objects tested in low temperature can be heated up in the dry environment and sent out of the dry environment after the heat-up. That is, there is no need to prepare another device for the heat-up, which saves costs and spaces.

BRIEF DESCRIPTION OF THE DRAWINGS

Other features and advantages of this invention will become more apparent in the following detailed description of the preferred embodiments of this invention, with reference to the accompanying drawings.

DETAILED DESCRIPTION OF THE PREFERRED EMBODIMENT

The present invention relates to a test apparatus. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
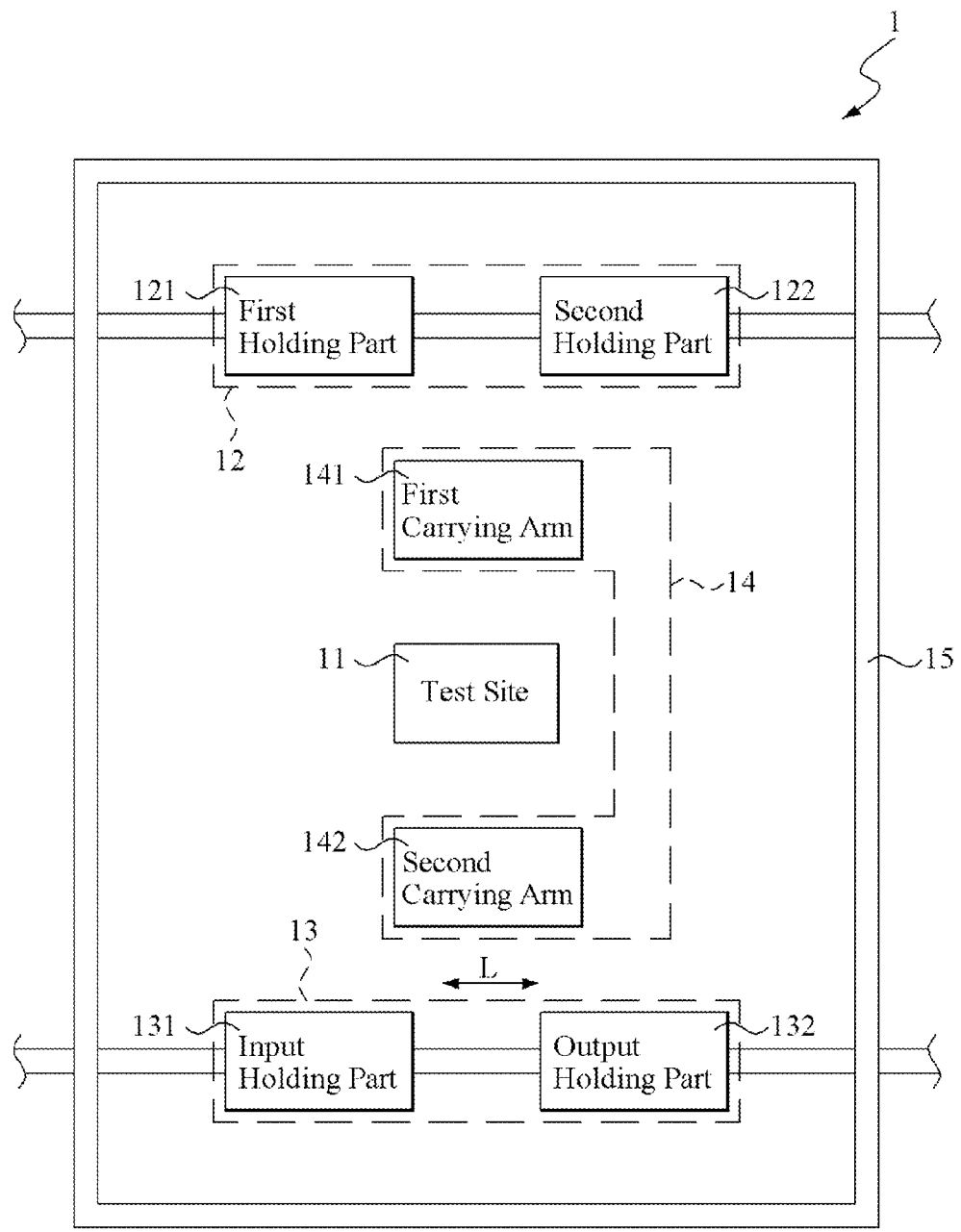
FIG. 1 is a schematic view of a test apparatus with dry environment according to the first embodiment of the present invention.

Refer to FIG. 1, a schematic view of a test apparatus with dry environment according to the first embodiment of the present invention. A test apparatus 1 with dry environment is provided according to the first embodiment of the present invention. The test apparatus 1 comprises a test site 11, a buffer carrying device 12, a transport carrying device 13, a handling mechanism 14 and a dry air flow guide mechanism 15. The buffer carrying device 12 is disposed close to a side of the test site 11, comprises a first holding part 121 and a second holding part 122. Besides, the buffer carrying device 12 comprises a temperature controller (not shown) of a thermo electric cooling (TEC) device. According to the first embodiment of the present invention, the temperature controller is disposed in the first holding part 121 and the second holding part 122. The temperature controller is selected from various cooling devices in other embodiments of the present invention.

The transport carrying device 13 is disposed close to another side of the test site 11 and comprises an input holding part 131 and an output holding part 132. The transport carrying device 13 further comprises a position mechanism (not shown) performing a position adjustment on the objects 2 (refer to FIG. 2 for the numeral). The position mechanism is disposed in the input holding part 131 and the output holding part 132. The output holding part 132 comprises a heat-up device (not shown) selected from various heating devices in the market, preferably with functions of regulating and increasing the temperature. The handling mechanism 14 comprises a first carrying arm 141 and a second carrying arm 142. The first carrying arm 141 and the second carrying arm 142 comprise robotic arms. Although the first carrying arm 141 and the second carrying arm 142 are illustrated as not connecting with the test apparatus 1 in the figure, it is only for schematic views; thus, the relative connections and positions thereof should depend on practical utilization and should not be limited by the figures.

The dry air flow guide mechanism 15 is disposed around the test site 11, the buffer carrying device 12, the transport carrying device 13 and the handling mechanism 14 and connects a dry air generation device (not shown). The dry air flow guide mechanism 15 illustrated in the figure is only for schematic views.

The test apparatus 1 tests the objects 2. The objects 2 comprise epitaxial wafers and other electronic components to be tested. According to the first embodiment of the present invention, the objects 2 are integrated circuit (IC) components. The buffer carrying device 12 holds the objects and performs the temperature conditioning process on the objects 2, wherein the temperature conditioning process comprises pre-cooling or pre-heating. According to the first embodiment of the present invention, the objects are conditioned from 0° C. to −55° C.; the temperature is set by a user on the test apparatus 1. Besides, the buffer carrying device 12 moves back and forth along a transporting direction L for the handling mechanism 14 to carry the objects 2 to the first holding part 121 and the second holding part 122.

The transport carrying device 13 moves back and forth along the transporting direction L, transporting the objects 2 approaching to and away from the test site 11. The transport carrying device 13 transports the objects 2 to the test site 11 via the input holding part 131. After testing, the transport carrying device 13 transports the objects 2 to the output holding part 132 from the test site 11. The transport carrying device 13 performs a temperature recovery process on the objects 2 until reaching or exceeding an ambient temperature. The temperature is set by the user on the test apparatus 1.

The handling mechanism 14 carries the objects 2 from the input holding part 131 to the buffer carrying device 12 for the temperature conditioning process and carries the objects 2 from the test site 11 to the output holding part 132 for the heat-up. Further, the first carrying arm 141 of the handling mechanism 14 carries the objects 2 from the transport carrying device 13 to the buffer carrying device 12 for the temperature conditioning process, carries the objects 2 from the buffer carrying device 12 to the test site 11 for the test procedure (the test procedure includes usual tests of electric property or other tests and is not further described here), and carries the objects 2 from the test site 11 to the transport carrying device 13 for the heat-up. Also, the second carrying arm 142 of the handling mechanism 14 carries the objects 2 from the transport carrying device 13 to the buffer carrying device 12 for the temperature conditioning process, carries the objects 2 from the buffer carrying device 12 to the test site 11 for the test procedure, and carries the objects 2 from the test site 11 to the transport carrying device 13 for the heat-up. The dry air flow guide mechanism 15 prevents the test apparatus from dew condensation and creates a dry environment.

Figure 2:
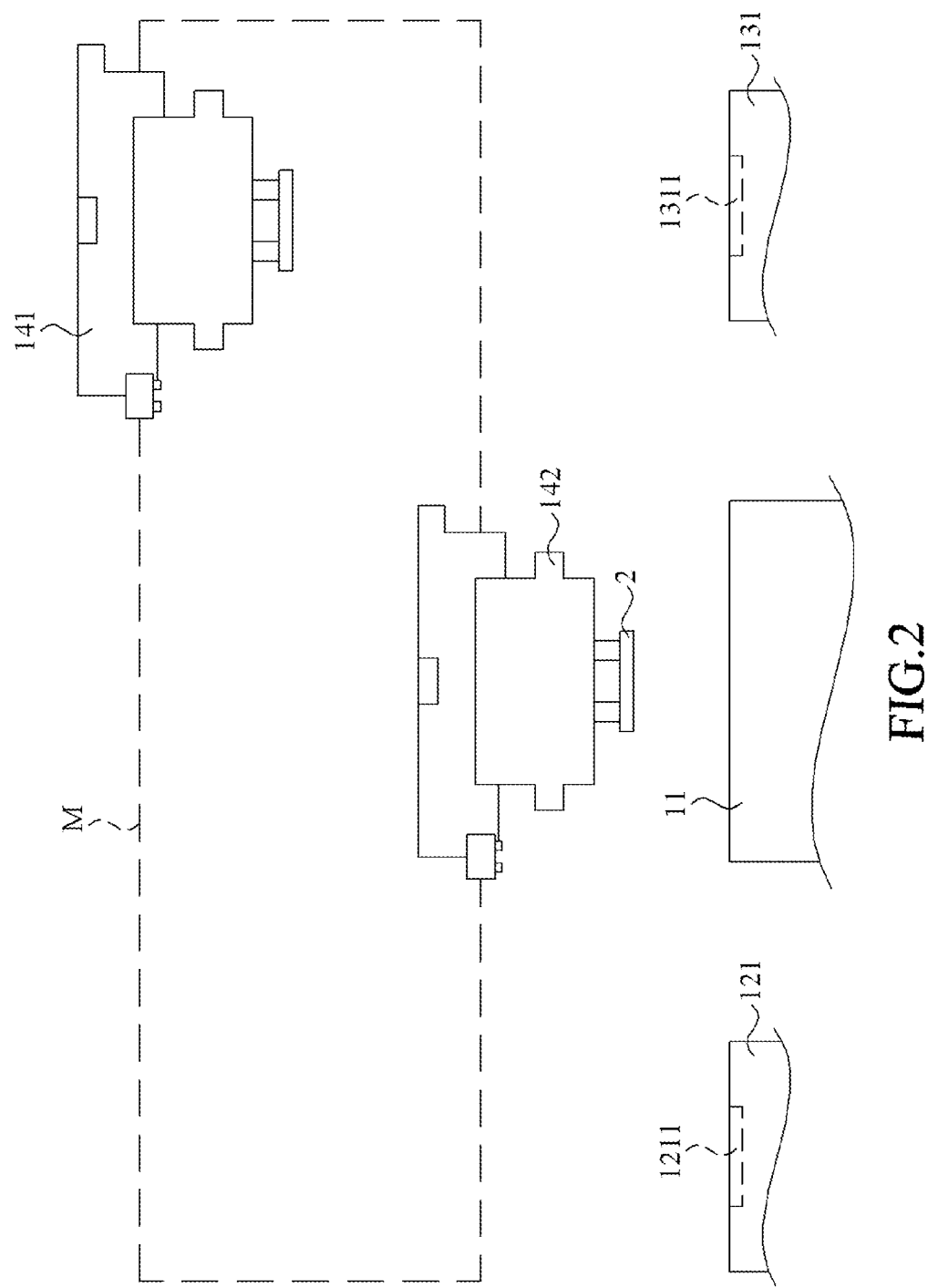
FIG. 2 is a schematic view showing a carrying route of a first carrying arm and a second carrying arm according to the first embodiment of the present invention.
Figure 3:
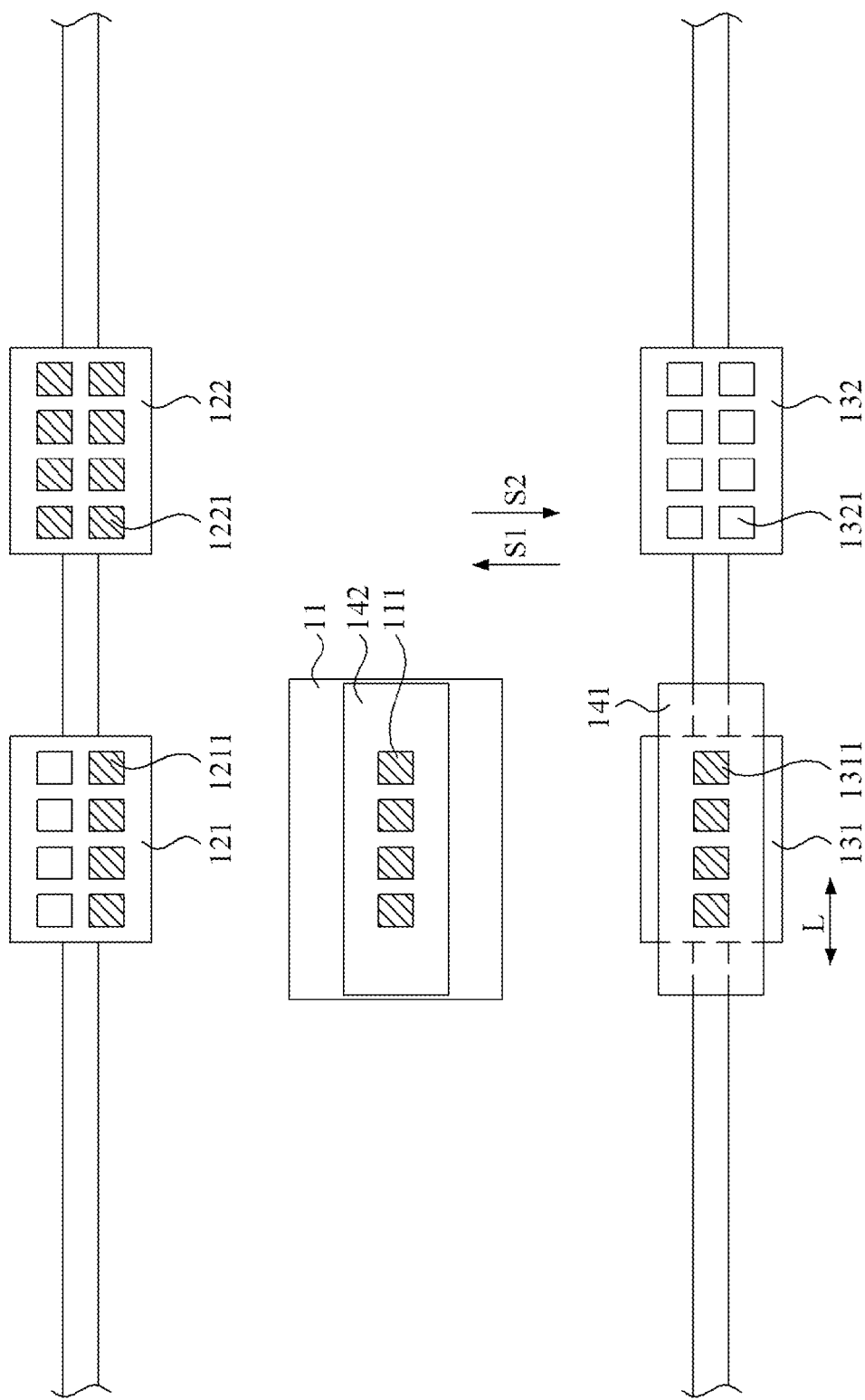
FIG. 3 to FIG. 3F are schematic views showing a handling mechanism carrying objects according to the first embodiment of the present invention.
Figure 3D:
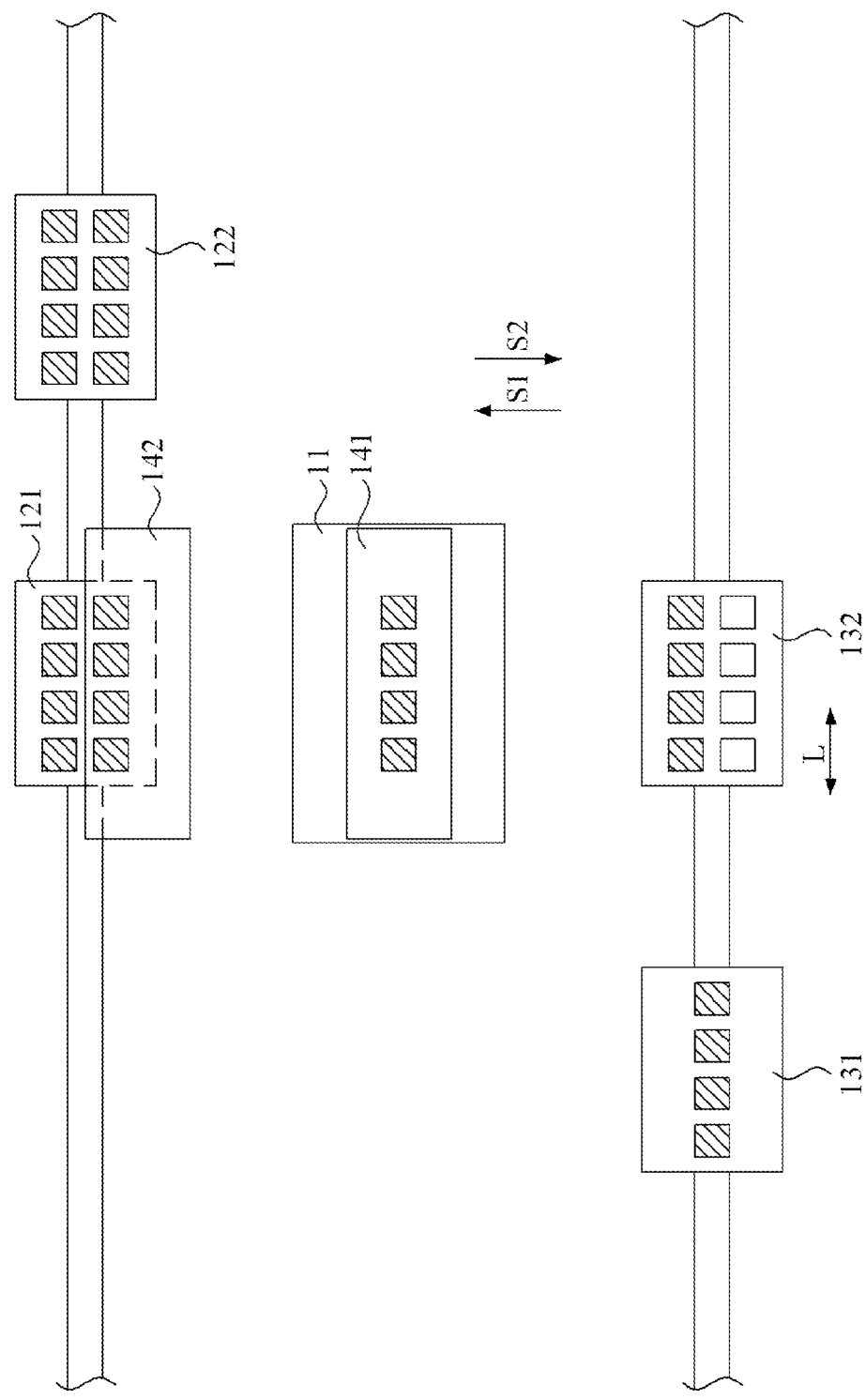
Figure 3E:
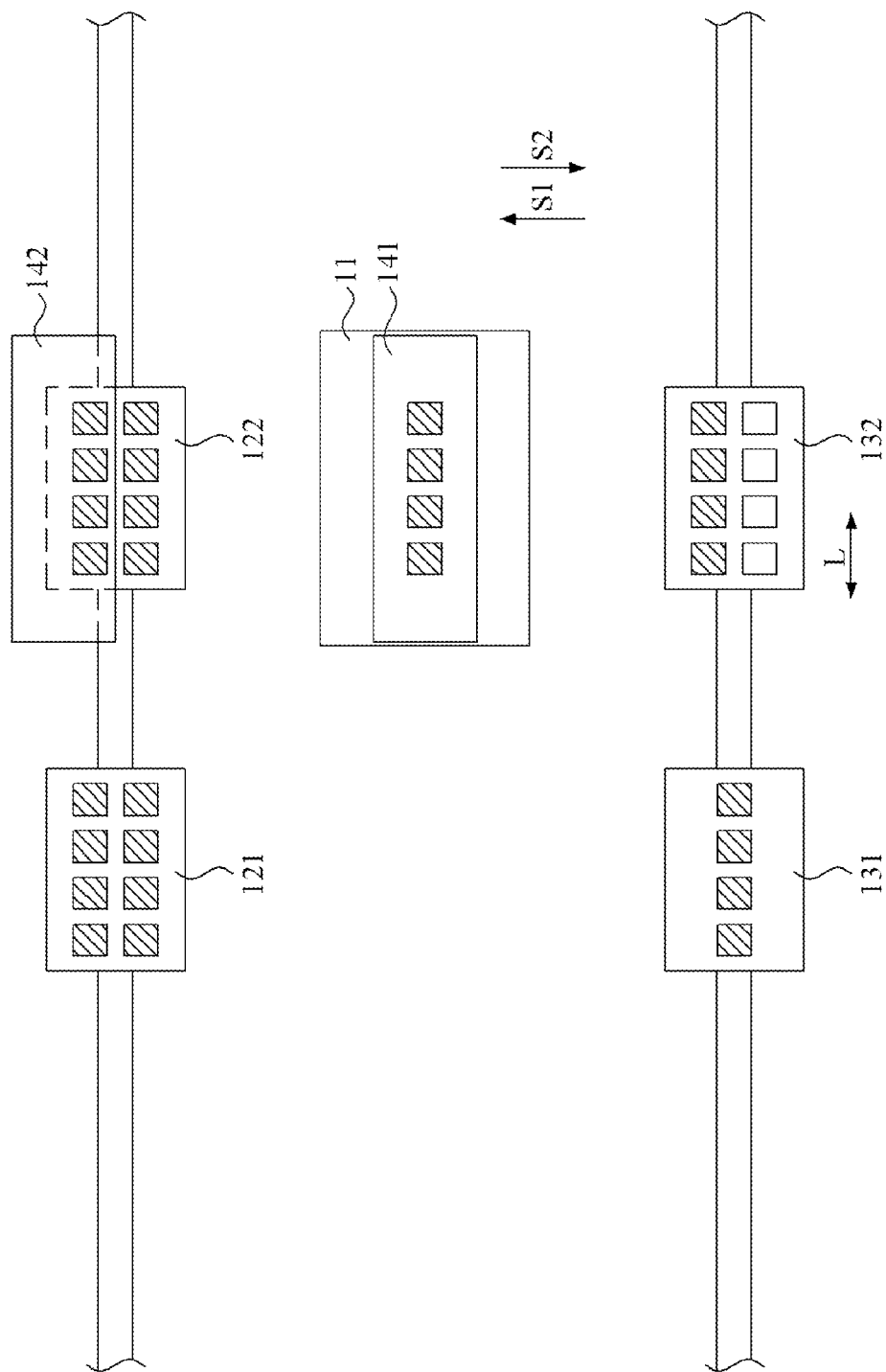
Figure 3F:
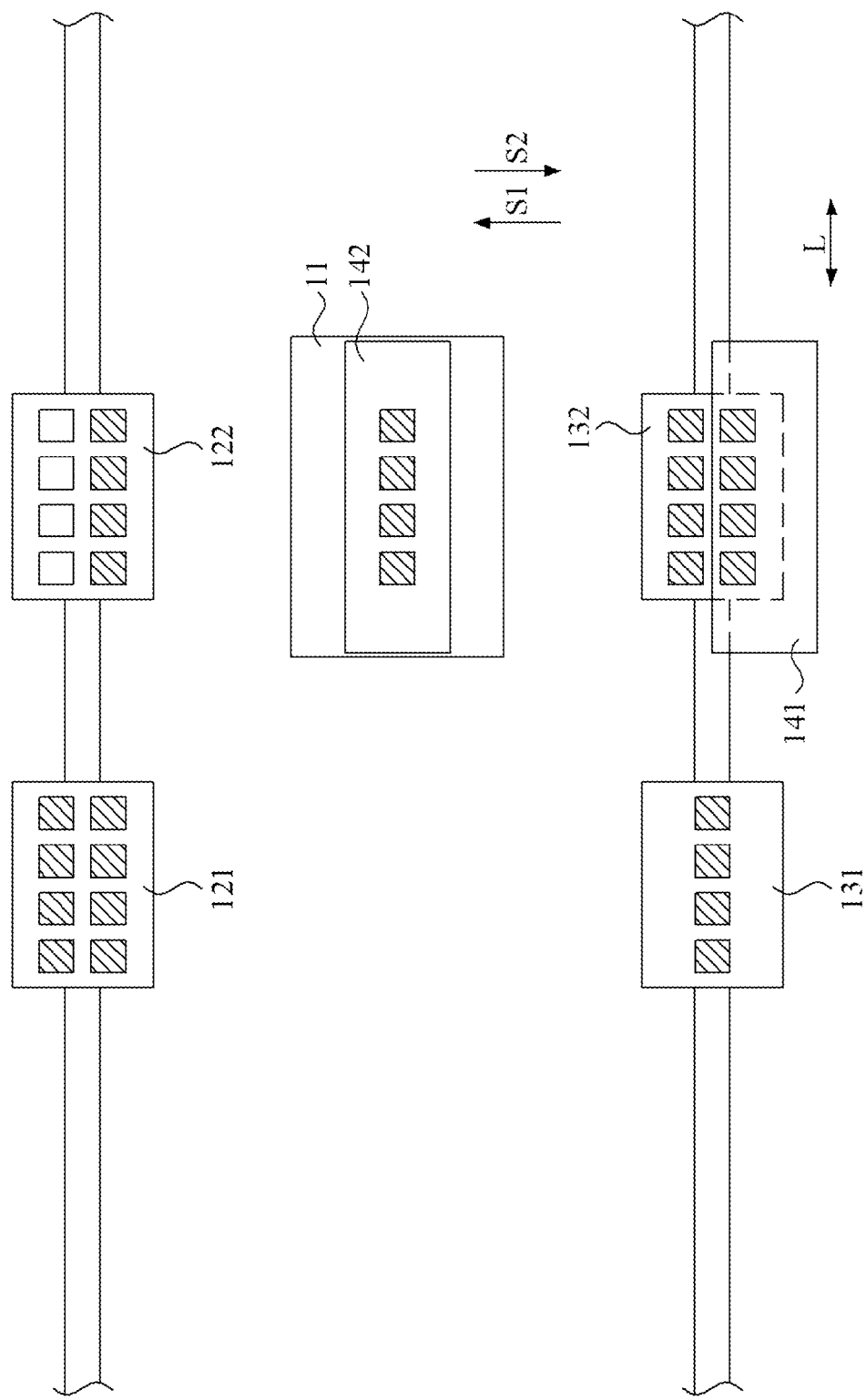

To describe how the handling mechanism 14 works more clearly, please refer to FIGS. 2, 3, 3A, 3B, 3C, 3D, 3E and 3F. FIG. 2 is a schematic view showing a carrying route of the first carrying arm and the second carrying arm according to the first embodiment of the present invention; FIG. 3 to FIG. 3F are schematic views showing the handling mechanism carrying objects according to the first embodiment of the present invention. It is to be noted that the buffer carrying device 12 and the transport carrying device 13 can only move back and forth repeatedly along the transporting direction L (i.e. moving back and forth along the direction of X-axis), while the first carrying arm 141 and second carrying arm 142 of the handling mechanism 14 can only move back and forth repeatedly along a carrying direction S1 and a carrying direction S2 (as shown from FIG. 3 to FIG. 3F); more accurately speaking, the first carrying arm 141 and second carrying arm 142 of the handling mechanism 14 can only move along a carrying route M (i.e. moving along the direction of Y-axis and Z-axis).

From FIG. 3 to FIG. 3F, the test site 11 comprises four test slots 111 (only one is identified with numeral); the first holding part 121 comprises eight holding slots 1211 (only one is identified with numeral); the second holding part 122 comprises eight holding slots 1221 (only one is identified with numeral); the input holding part 131 comprises four holding slots 1311 (only one is identified with numeral); the output holding part 132 comprises eight slots 1321 (only one is identified with numeral); the diagonals illustrated in the figures show that the test slots 1111 and holding slots 1211, 1221, 1311 and 1321 holding the objects 2 (i.e. IC components).

Refer to FIG. 3 more thoroughly. Initially, the first carrying arm 141 carries the objects 2 along the carrying direction S2 from the transport carrying device 121 to the holding slots 1311 of the input holding part 141; meanwhile, the second carrying arm 142 stays in the test site 11, waiting the test procedure to finish. Refer to FIG. 3A. After the first carrying arm 141 carries the objects 2 (how the objects 2 are carried is a common technique and is not mentioned redundantly), moves along the carrying direction S1 to the first holding part 121 of the buffer carrying device 12, and puts the objects 2 in upper holding slots 1211 as illustrated for the temperature conditioning process, the second carrying arm 142 is still in the test site 11, waiting the test procedure to finish. The input holding part 131 and the output holding part 142 move toward left along the transporting direction L (i.e. the direction of −X-axis) so that the input holding part 131 receives the objects 2 to be tested.

Refer to FIG. 3B. After the first carrying arm 141 puts the objects 2, the first carrying arm 141 immediately takes the objects 2 in the lower holding slots 1211 of the first holding part 121 and moves along the carrying direction S2 to the test site 11 in order to put the objects 2 in the test slots 111; meanwhile, the second carrying arm 142 carries the objects 2 tested from the test slot slots 111 along the carrying direction S2 to the upper holding slots 1321 of the output holding part 132 for the heat-up. (i.e. When the first carrying arm 141 moves from the buffer carrying device 12 to the test site 11, the second carrying arm 142 moves from the test site 11 to the transport carrying device 13. The buffer carrying device 12 does not move; its position in FIG. 3B is similar to FIG. 3A.)

Refer to FIG. 3C. After the second carrying arm 142 finishes carrying, the input holding part 131 and the output holding part 132 move toward right along the transporting direction L (i.e. the direction of X-axis) so that the second carrying arm 142 carries the objects in the input holding part 131; meanwhile, the first carrying arm 141 is still in the test site 11, waiting for the test procedure to finish. (The buffer carrying device 12 does not move; its position in FIG. 3C is similar to FIG. 3B.)

Refer to FIG. 3D. After the second carrying arm 142 takes the objects 2 in the input holding part 131, it moves toward the carrying direction S1 to the lower holding slots 1211 of the first holding part 121 to put the objects 2 in the lower holding slots 1211 for the temperature conditioning process; meanwhile, the first carrying arm 141 is still in the test site, waiting for the test procedure to finish. The input holding part 131 and the output holding part 132 move toward left along the transporting direction (i.e. the direction of −X-axis) so the input holding part 131 receives the objects 2 to be tested.

Refer to FIG. 3E. After the second carrying arm 142 puts the objects 2 tested, the first holding part 121 and the second holding part 122 move toward left (i.e. the direction of −X-axis) along the transporting direction L so the second carrying arm 142 takes the objects in the upper slots 1221 of the second holding part 122; meanwhile, the first carrying arm 141 is still in the test site, waiting for the test procedure to finish.

Refer to FIG. 3F. After the second carrying arm 142 takes the objects 2 in the upper slots 1221 of the second holding part 122, it moves along the carrying direction S2 to the test site 11 in order to put the objects 2 in the test slots 111; meanwhile, the first carrying arm 142 carries the objects tested from the test slots 111 along the carrying direction S2 to the lower holding slots 1321 of the output holding part 132 for the heat-up. (The buffer carrying device 12 does not move; its position in FIG. 3F is similar to FIG. 3E.) At last, the input holding part 131 and the output holding part 132 move toward right along the transporting direction L (i.e. the direction of X-axis). It should be noted that the whole process of carrying is only according to the first embodiment of the present invention and thus should not limit the process and route in other embodiments of the present invention.

Figure 4:
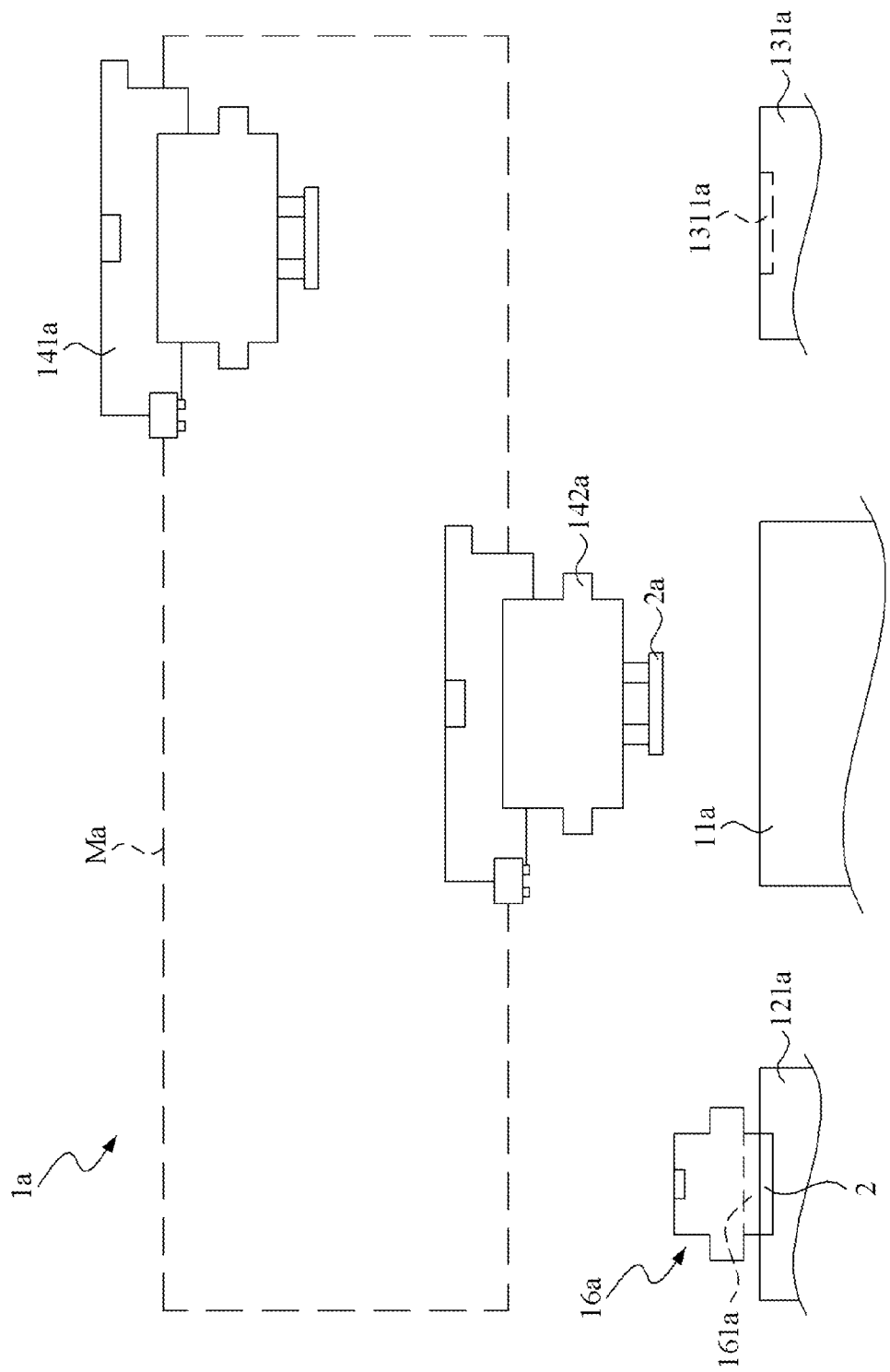
FIG. 4 is a schematic view showing a first operation of a pressing mechanism according to the second embodiment of the present invention.
Figure 4A:
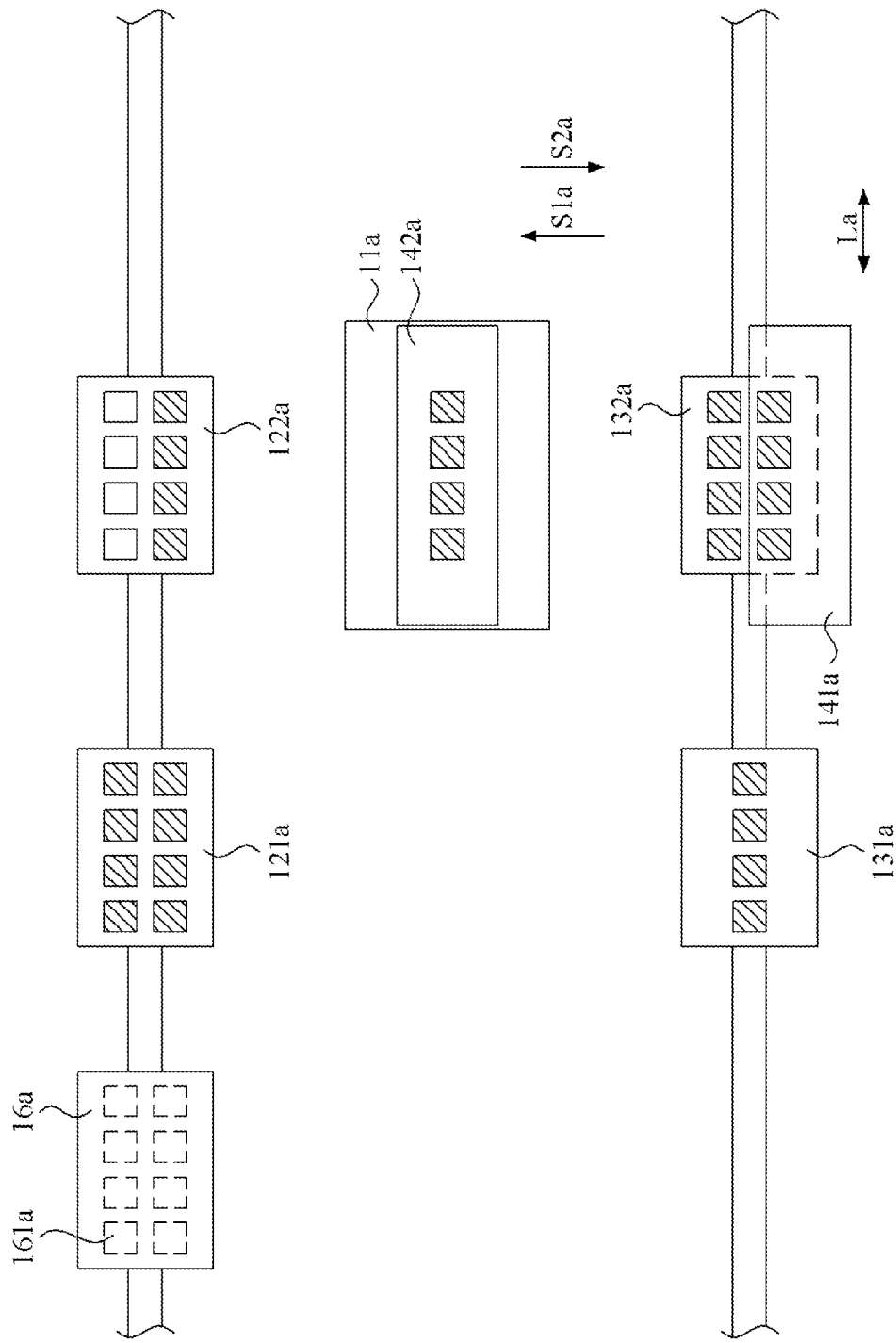
FIG. 4A is a schematic view showing a second operation of the pressing mechanism according to the second embodiment of the present invention.

Refer to FIGS. 4 and 4A; FIG. 4 is a schematic view showing a first operation of a pressing mechanism according to the second embodiment of the present invention; FIG. 4A is a schematic view showing a second operation of the pressing mechanism according to the second embodiment of the present invention. A test apparatus 1a further comprises a pressing mechanism 16a performing the temperature conditioning process on surfaces of objects 2a held in a buffer carrying device (not shown) by installing a temperature controller in the pressing mechanism 16a.

Besides, the pressing mechanism 16a comprises a plurality of contact devices 161a (only one is identified with numeral). According to the second embodiment of the present invention, the contact devices 161a contact the surfaces of the objects 2a to perform the temperature conditioning process. A first carrying arm 141a and a second carrying arm 142a move along a carrying direction S1a and a carrying direction S2a. That is, the first carrying arm 141a and the second carrying arm 142a move along a carrying route Ma as shown in FIG. 4.

The pressing mechanism 16a can move only up and down to perform the temperature conditioning process on the surfaces of the objects 2a when the buffer carrying device moves to the relative position. Besides, the pressing mechanism 16a can moves along a transporting direction La as shown in FIG. 4A. After the objects 2a are put in holding slots 1211a, the pressing mechanism 16a moves above the objects 2a and presses down on the surface of the objects so that the contact devices 161a contact the surfaces of the objects 2a to perform the temperature conditioning process.

According to the second embodiment of the present invention, the pressing mechanism 16a and the first holding part 121a or the second holding part 122a of the buffer carrying device perform the temperature conditioning process on the objects 2a simultaneously so that both the upper and lower surfaces of the objects 2a are regulated at the same time; as a result, the temperature conditioning process is faster and more even.

In conclusion, the test apparatus 1 according to the first embodiment of the present invention can perform the temperature conditioning process and has a dry environment for test. Therefore, the temperature of the objects has been conditioned before tests, which saves time for waiting the objects to be cooled. Besides, the dry air flow guide mechanism 15 creates a dry environment for the test apparatus 1 to prevent dew condensation and icing. Moreover, the test apparatus 1 further comprises the function of heat-up so the objects tested in low temperature can be heated up in the dry environment and sent out of the dry environment after the heat-up. That is, there is no need to prepare another device for the heat-up, which saves costs and spaces.

While the present invention has been particularly shown and described with reference to a preferred embodiment, it will be understood by those skilled in the art that various changes in form and detail may be without departing from the spirit and scope of the present invention.

What is claimed is:

1. A test apparatus with dry environment for testing a plurality of objects, the test apparatus comprising:
   a test site performing a test procedure on the objects;
   a buffer carrying device disposed close to a side of the test site, the buffer carrying device holding the objects and performing a temperature conditioning process on the objects;
   a transport carrying device disposed close to another side of the test site and disposed movably back and forth along a transporting direction, the transport carrying device transporting the objects approaching to and away from the test site and performing a temperature recovery process on the objects;
   a handling mechanism carrying the objects to the buffer carrying device, to the test site and to the transport carrying device; and
   a dry air flow guide mechanism guiding a dry air to surround the test site, the buffer carrying device, the transport carrying device and the handling mechanism so as to prevent the dry environment from dew condensation;
   wherein the handling mechanism comprises a first carrying arm carrying the objects from the transport carrying device to the buffer carrying device for performing the temperature conditioning process, carrying the objects from the buffer carrying device to the test site for performing the test procedure, and carrying the objects from the test site to the transport carrying device for performing the temperature recovery process; and
   wherein the handling mechanism further comprises a second carrying arm carrying the objects from the transport carrying device to the buffer carrying device for performing the temperature conditioning process, carrying the objects from the buffer carrying device to the test site for performing the test procedure, and carrying the objects from the test site to the transport carrying device for performing the temperature recovery process.

2. The test apparatus according to claim 1, wherein when the first carrying arm moves from the transport carrying device to the buffer carrying device, the second carrying arm stays at the test site for performing the test procedure or waits; when the first carrying arm moves from the buffer carrying device to the test site, the second carrying arm moves from the test site to the transport carrying device.

3. The test apparatus according to claim 1, wherein the transport device comprises an input holding part and an output holding part; the handling mechanism carries the objects from the input holding part to the buffer carrying device for performing the temperature conditioning process and carries the objects from the test site to the output holding part for performing the temperature recovery process.

4. The test apparatus according to claim 3, wherein the output holding part comprises a heat-up device performing the temperature recovery process.

5. The test apparatus according to claim 1, wherein the buffer carrying device comprises a plurality of holding parts, the buffer carrying device moving back and forth along the transporting direction for the handling mechanism carrying the objects to the holding parts individually.

6. The test apparatus according to claim 1, wherein the buffer carrying device comprises a temperature controller performing the temperature conditioning process.

7. A test apparatus with dry environment for testing a plurality of objects, the test apparatus comprising:
   a test site performing a test procedure on the objects;
   a buffer carrying device disposed close to a side of the test site, the buffer carrying device holding the objects and performing a temperature conditioning process on the objects;
   a transport carrying device disposed close to another side of the test site and disposed movably back and forth along a transporting direction, the transport carrying device transporting the objects approaching to and away from the test site and performing a temperature recovery process on the objects;
   a handling mechanism carrying the objects to the buffer carrying device, to the test site and to the transport carrying device;
   a dry air flow guide mechanism guiding a dry air to surround the test site, the buffer carrying device, the transport carrying device and the handling mechanism so as to prevent the dry environment from dew condensation; and
   a pressing mechanism performing the temperature conditioning process on surfaces of the objects held in the buffer carrying device.

* * * * *